(12) United States Patent
Kitano

(10) Patent No.: US 8,814,783 B2
(45) Date of Patent: Aug. 26, 2014

(54) ILLUMINATION LENS AND ENDOSCOPE

(75) Inventor: Ryo Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 469 days.

(21) Appl. No.: 13/017,178

(22) Filed: Jan. 31, 2011

(65) Prior Publication Data
US 2011/0245617 A1   Oct. 6, 2011

(30) Foreign Application Priority Data

Mar. 31, 2010   (JP) ................. 2010-084427

(51) Int. Cl.
*A61B 1/06*   (2006.01)

(52) U.S. Cl.
USPC ............... 600/177; 600/176; 600/160

(58) Field of Classification Search
None
See application file for complete search history.

(56) References Cited

U.S. PATENT DOCUMENTS

| | | | |
|---|---|---|---|
| 4,415,240 A | | 11/1983 | Nishioka et al. |
| 4,807,597 A | * | 2/1989 | Tsuno et al. ............... 600/177 |
| 6,206,825 B1 | * | 3/2001 | Tsuyuki ..................... 600/182 |
| 6,533,722 B2 | * | 3/2003 | Nakashima ................ 600/179 |
| 6,569,088 B2 | * | 5/2003 | Koshikawa ................ 600/177 |
| 6,905,462 B1 | * | 6/2005 | Homma et al. ............ 600/176 |
| 6,994,668 B2 | * | 2/2006 | Miyano ...................... 600/176 |
| 7,338,439 B2 | * | 3/2008 | Kanai ......................... 600/176 |
| 7,585,274 B2 | * | 9/2009 | Homma ...................... 600/160 |
| 7,701,650 B2 | * | 4/2010 | Lin ............................. 359/793 |
| 7,794,397 B2 | * | 9/2010 | Takase et al. .............. 600/182 |
| 7,981,027 B2 | * | 7/2011 | Miyagi et al. .............. 600/129 |
| 8,118,734 B2 | * | 2/2012 | Murayama ................. 600/177 |
| 2004/0242963 A1 | * | 12/2004 | Matsumoto et al. ....... 600/127 |
| 2005/0256377 A1 | * | 11/2005 | Deppmeier et al. ....... 600/176 |
| 2007/0118020 A1 | * | 5/2007 | Miyagi et al. .............. 600/177 |
| 2009/0306478 A1 | * | 12/2009 | Mizuyoshi ................. 600/178 |

FOREIGN PATENT DOCUMENTS

| | | |
|---|---|---|
| JP | 56-020428 A | 2/1981 |
| JP | 60-262120 A | 12/1985 |
| JP | 2000-193894 A | 7/2000 |

OTHER PUBLICATIONS

Office Action, dated Dec. 10, 2013, issued by the Japanese Patent Office, in counterpart Application No. 2010-084427.

* cited by examiner

*Primary Examiner* — Anhtuan T Nguyen
*Assistant Examiner* — Jae Woo
(74) *Attorney, Agent, or Firm* — Sughrue Mion, PLLC

(57) ABSTRACT

An illumination lens to be disposed in a front end of a light guide of an endoscope includes an entrance face and an exit face. The entrance face has positive power. The exit face has positive power. The following Expression (1) is satisfied while the following Expression (2) is satisfied.

$$1.2 < 1/r_1 \times \phi < 1.8, \quad (1)$$

$$0.24 < 1/r_2 \times \phi < 0.96, \quad (2)$$

where $\phi$ [mm] is a diameter of the lens, $r_1$ [mm] is a curvature radius of the entrance face, and $r_2$ [mm] is a curvature radius of the exit face.

6 Claims, 6 Drawing Sheets

US 8,814,783 B2

ILLUMINATION LENS AND ENDOSCOPE

CROSS-REFERENCE TO RELATED APPLICATIONS

This application is based upon and claims the benefit of priority from Japanese Patent Application No. 2010-084427, filed Mar. 31, 2010, the entire contents of which are incorporated herein by reference.

BACKGROUND

1. Technical Field

The present invention relates to an illumination lens disposed in a front end of a light guide of an endoscope, and an endoscope provided with the illumination lens disposed in a front end of a light guide.

2. Related Art

In the background art, an illumination optical system of an endoscope is typically constituted by a concave lens disposed in a front end of a light guide for guiding illumination light, so that the illumination light emitted from the light guide can be refracted outward and diffused. With such a configuration, light rays are kicked on the side face of the lens. Thus, loss in the quantity of light is comparatively large in the periphery of an irradiation field.

There has been therefore a proposal that a lens whose entrance face is formed as a convex face with positive power is disposed in a front end of a light guide (for example, see JP-A-2000-193894). With such a configuration, illumination light emitted from the light guide is once collected (refracted inward) by the lens and then diffused so that light rays can be prevented from being kicked on the side face of the lens. Thus, improvement in utilization efficiency of the illumination light can be expected.

In view of the design of the lens, however, there is a limit on wide-angle light distribution which can be obtained by the lens whose entrance face is formed as a convex face with positive power, even when the entrance face is made aspherical. The entrance face of the illumination lens described in JP-A-2000-193894 is formed as a light diffusing face in order to cancel unevenness in light distribution. According to JP-A-2000-193894, wider-angle light distribution can be expected by a diffusion effect while unevenness in the light distribution can be cancelled. However, there is a fear that the utilization efficiency of the illumination light improved by the entrance face formed as a convex face with positive power may deteriorate due to the diffusion.

In recent years, heat capacity of an endoscope has decreased with reduction in the diameter of the endoscope, and power consumption of the endoscope has increased with increase in the number of pixels in an image sensor mounted in the endoscope. It has been therefore indispensable to take measures to suppress temperature rise in a front portion of an insertion portion. Illumination light also becomes a heat source. However, the quantity of illumination light can be suppressed if the utilization efficiency of the illumination light can be improved. Thus, heat caused by the illumination light can be cut off to suppress temperature rise in the front end portion of the insertion portion.

The invention was developed in consideration of the aforementioned circumstances. An object of the invention is to improve the utilization efficiency of illumination light and achieve wider-angle light distribution in an illumination lens disposed in a front end of a light guide of an endoscope.

SUMMARY OF THE INVENTION

According to an aspect of the invention, an illumination lens to be disposed in a front end of a light guide of an endoscope includes an entrance face and an exit face. The entrance face has positive power. The exit face has positive power. The following Expression (1) is satisfied while the following Expression (2) is satisfied.

$$1.2 < 1/r_1 \times \phi < 1.8, \quad (1)$$

$$0.24 < 1/r_2 \times \phi < 0.96, \quad (2)$$

where $\phi$ [mm] is a diameter of the lens, $r_1$ [mm] is a curvature radius of the entrance face, and $r_2$ [mm] is a curvature radius of the exit face.

DETAILED DESCRIPTION

Figure 1:
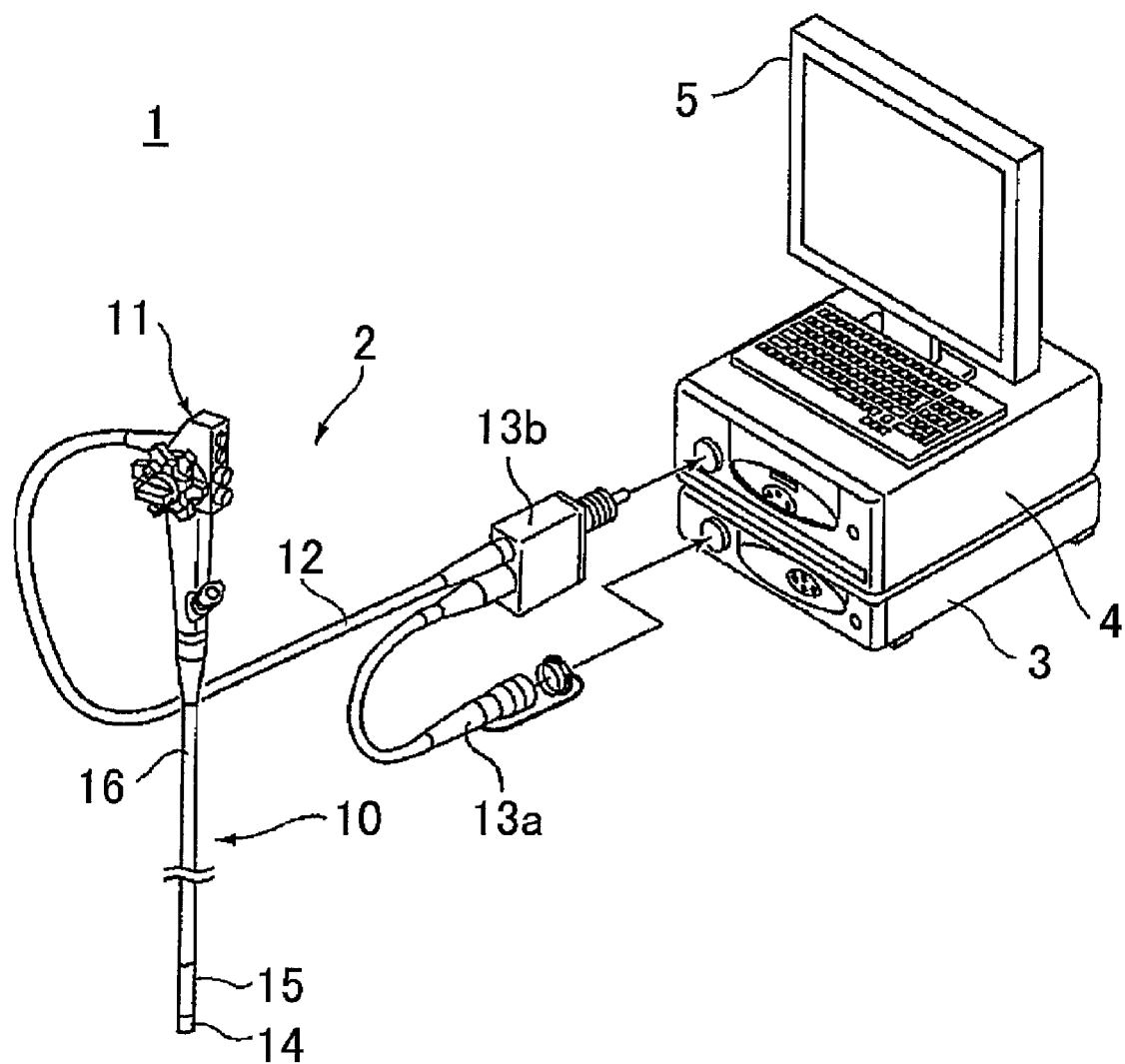
FIG. 1 is a view showing an example of an endoscope for explaining an exemplary embodiment of the invention.

FIG. 1 shows an example of an endoscope.

An endoscope 1 has an insertion portion 10 which will be inserted into a subject body, an operation portion 11 which is provided consecutively to the insertion portion 10, and a universal cord 12 which extends from the operation portion 11. The universal cord 12 contains a light guide, a signal line, etc. Connectors 13a and 13b are provided in a terminal end of the universal cord 12. The endoscope 1 is attached to a processor 3 through the connector 13a, and attached to a light source unit 4 through the connector 13b.

The insertion portion 10 has a front end portion 14, a curved portion 15 which is provided consecutively to a proximal end side of the front end portion 14, and a flexible portion 16 which connects the curved portion 15 with the operation portion 11. The curved portion 15 is formed so that the curved portion 15 can be bent up, down, right and left. Bending of the curved portion 15 is operated by the operation portion 11. The light guide and the signal line contained in the universal cord 12 reach the front end portion 14 via the operation portion 11, the flexible portion 16 and the curved portion 15.

Figure 2:
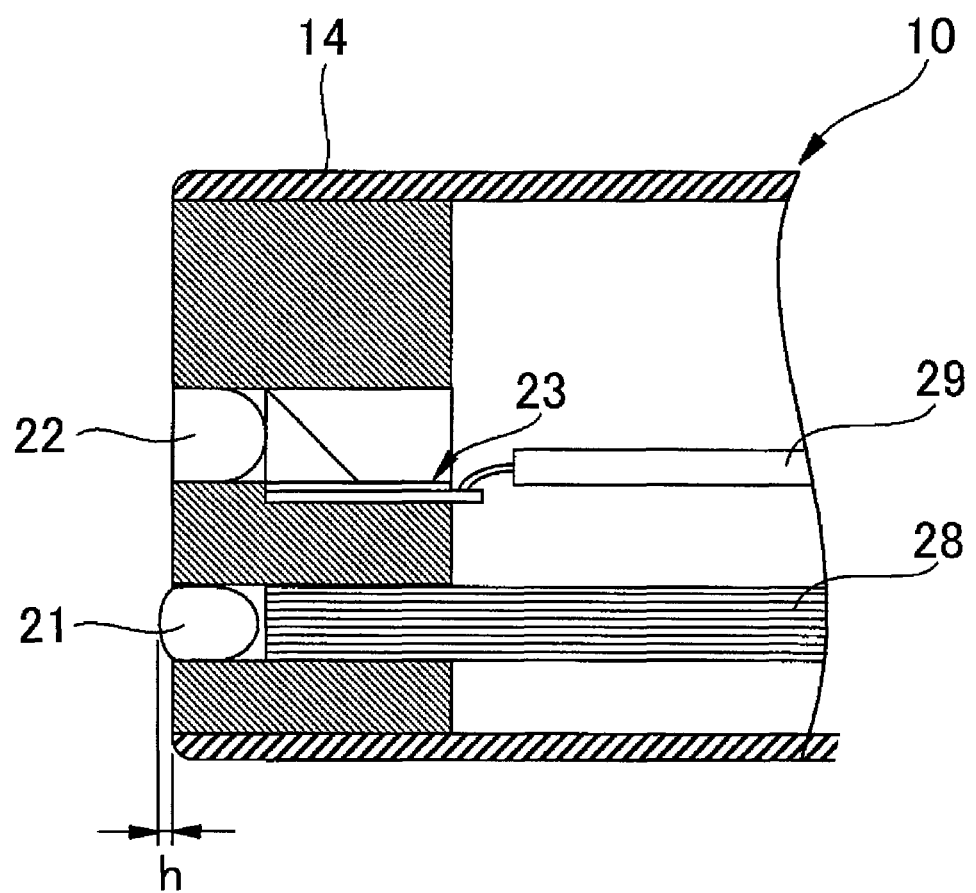
FIG. 2 is a sectional view showing a front end portion of an insertion portion of the endoscope in FIG. 1.

FIG. 2 shows the front end portion 14 of the insertion portion 10 of the endoscope 1 in section.

The front end portion 14 includes an illumination lens 21, an imaging unit 23 and an objective lens 22. The illumination lens 21 emits illumination light toward a region to be observed. The imaging unit 23 includes a solid-state image sensor such as a CCD image sensor. The objective lens 22 collects feedback light from the region to be observed, and forms an image on an image reception face of the solid-state image sensor included in the imaging unit 23.

Illumination light generated by the light source unit 4 (see FIG. 1) is guided to the front end portion 14 through a light guide 28, and applied to the subject body by the illumination lens 21 disposed in the front end of the light guide 28. Feedback light from the subject body is collected by the objective lens 22, and an image is formed on the image reception face of the solid-state image sensor included in the imaging unit 23. An image signal of the subject body is generated by the imaging unit 23.

The image signal generated by the imaging unit 23 is sent to the processor 3 (see FIG. 1) through a signal line 29 connected to the imaging unit 23. For example, the processor 3 processes the supplied image signal to generate display image data. Based on the generated display image data, an image of the subject body is displayed on a monitor 5 (see FIG. 1)

Figure 3:
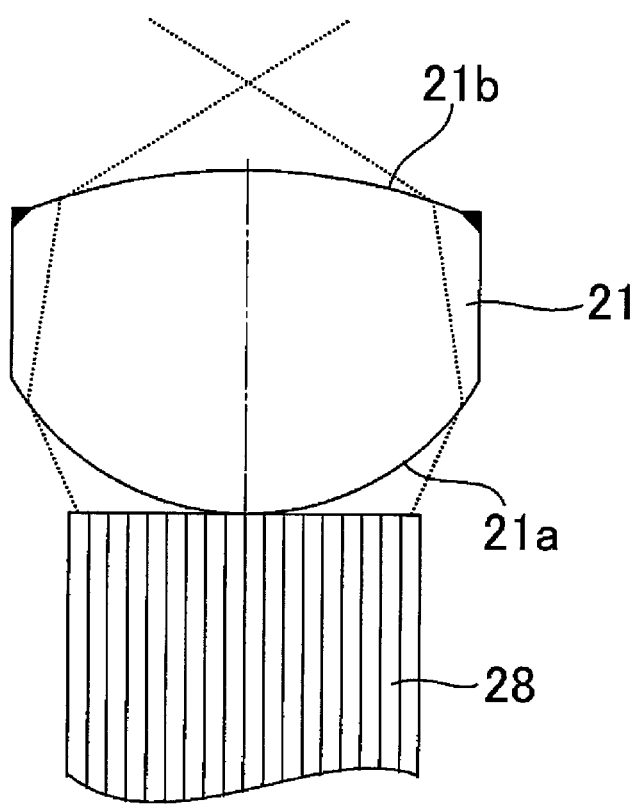
FIG. 3 is a view showing an illumination lens of the endoscope in FIG. 1.

FIG. 3 shows the illumination lens 21.

An entrance face 21a and an exit face 21b of the illumination lens 21 are formed as convex faces with positive power respectively. In the illumination lens 21 configured thus, illumination light incident on the entrance face 21a is once collected (refracted inward) and then diffused as described above.

In the depicted example, the entrance face 21a is formed as a light diffusing face. Thus, unevenness in distribution of the illumination light is reduced while the distribution of the illumination light is made wider in angle. The light diffusing face may be formed, for example, by graining based on polishing. The face roughness of the light diffusing face is typically not higher than several μm, preferably in a range of from 0.3 to 0.7 μm, in arithmetic average roughness Ra.

Figure 4:
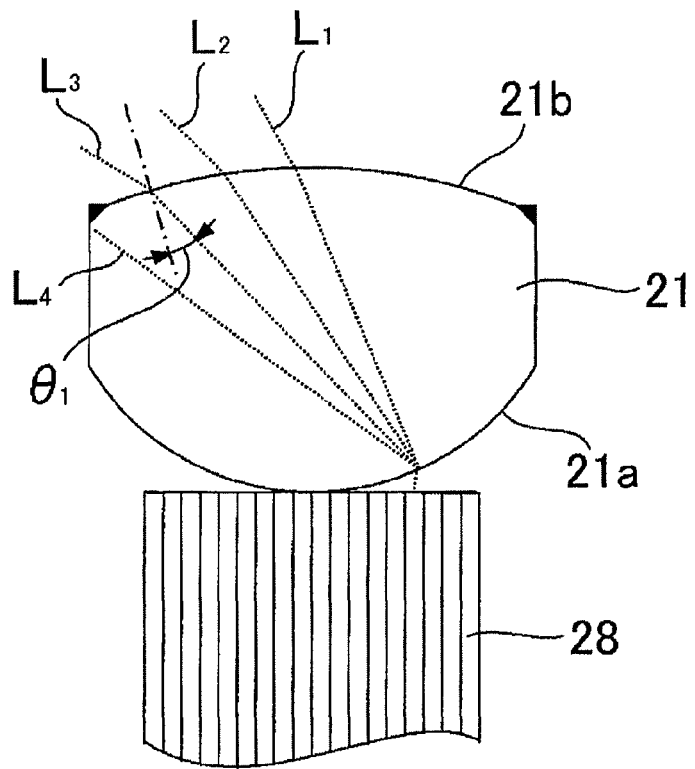
FIG. 4 is a schematic view showing the behavior of light rays in the illumination lens in FIG. 3.
Figure 5:
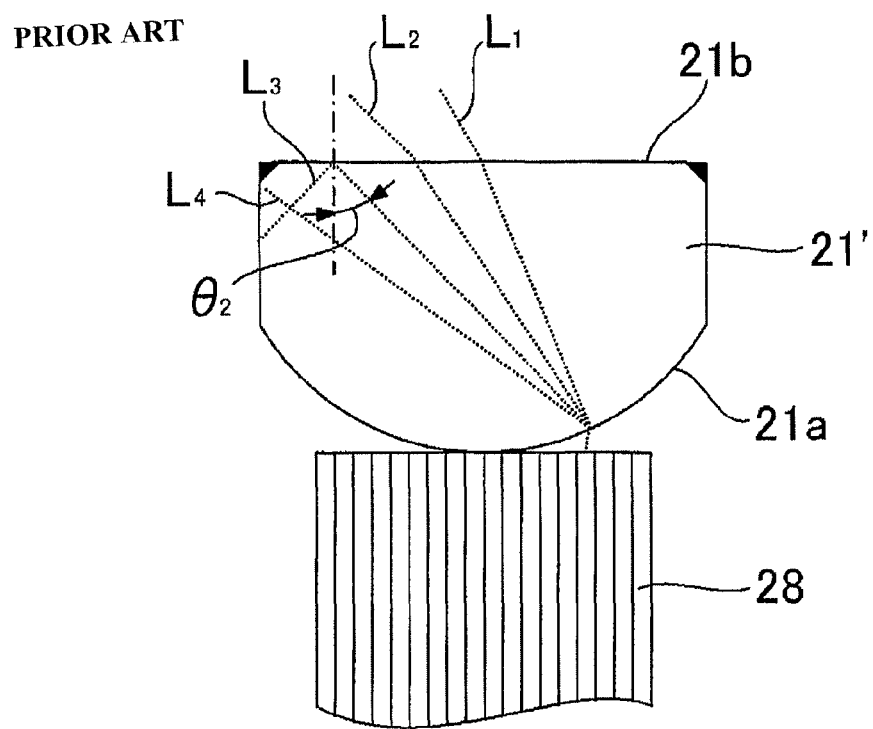
FIG. 5 is a schematic view showing the behavior of light rays in the illumination lens whose exit face is formed as a flat face.

FIG. 4 shows the behavior of light rays in the illumination lens 21. FIG. 5 shows the behavior of light rays in an illumination lens 21' whose exit face 21b is formed as a flat face for the purpose of explanation.

If the entrance face 21a is not set as a light diffusing face, a light ray incident on the entrance face 21a at an angle will be refracted at a unique angle and outgo from the exit face 21b as shown by $L_1$ in FIG. 4. Since the entrance face 21a is a light diffusing face, the light ray incident on the entrance face 21a at the angle is, for example, diffused as shown by $L_2$, $L_3$ and $L_4$.

The light ray $L_2$ outgoes from the exit face 21b in each of the illumination lenses 21 and 21'. This light ray $L_2$ contributes to illumination to make the light distribution wider in angle. On the other hand, in each of the illumination lenses 21 and 21', the light ray $L_4$ is kicked on the side face of the lens so as not to contribute to illumination.

In the illumination lens 21', the incident angle $\theta_2$ of the light ray $L_3$ on the flat exit face 21b is not smaller than a critical angle $\theta_c$. As a result, total reflection of the light ray $L_3$ occurs so that the light ray $L_3$ cannot outgo from the exit face 21b. Thus, the light ray $L_3$ does not contribute to illumination. On the other hand, in the illumination lens 21, the exit face 21b is formed as a convex face with positive power. The incident angle $\theta_1$ of the light ray $L_3$ on the exit face 21b is smaller than the critical angle $\theta_c$. As a result, total reflection of the light ray $L_3$ does not occur, but the light ray $L_3$ outgoes from the exit face 21b. Thus, the utilization efficiency of the illumination light can be improved, and the light distribution can be made further wider in angle.

EXAMPLE

Preferred numeric ranges of dimensions in the illumination lens 21 were obtained by calculation. In the following description, assume that the lens diameter φ is 1.2 [mm].

Figure 6:
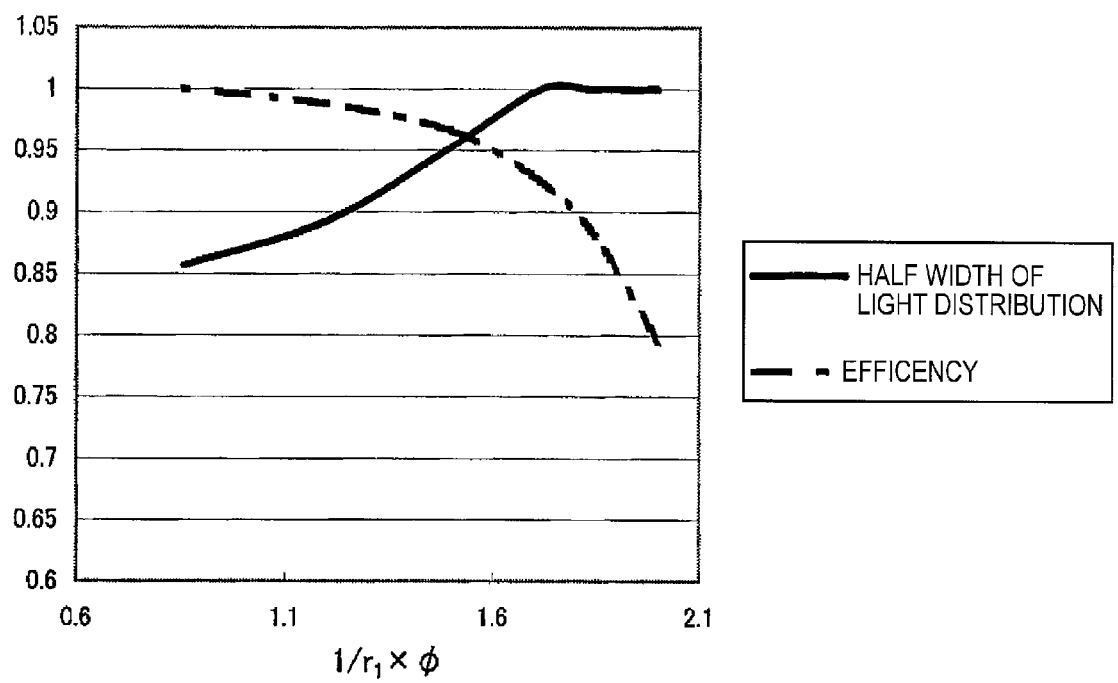
FIG. 6 is a graph showing the relation among the curvature radius of the entrance face of the illumination lens, the utilization efficiency of illumination light, and the half width of light distribution.

FIG. 6 shows the relation among the curvature radius $r_1$ of the entrance face 21a of the illumination lens 21, the utilization efficiency of illumination light, and the half width of light distribution. The curvature radius $r_1$ is normalized with the lens diameter φ. The efficiency herein is based on a result of the quantity of illumination light integrated all over the field of irradiation. Each of the efficiency and the half width of light distribution shows a saturation tendency. Thus, the efficiency and the half width of light distribution are normalized with their maximum saturation values respectively.

From FIG. 6, with decrease in the curvature radius $r_1$ of the entrance face 21a (or with increase of $1/r_1 \times \phi$), the half width of light distribution expands while the efficiency deteriorates. That is, there is a trade-off relation between improvement in the efficiency and the wider-angle light distribution. When $1/r_1 \times \phi$ satisfies the condition of $1.2 < 1/r_1 \times \phi < 1.8$, the efficiency and the half width of light distribution can be reduced within 10% relatively to their maximum saturation values respectively. Thus, a good balance can be achieved between improvement in the efficiency and the wider-angle light distribution.

Figure 7:
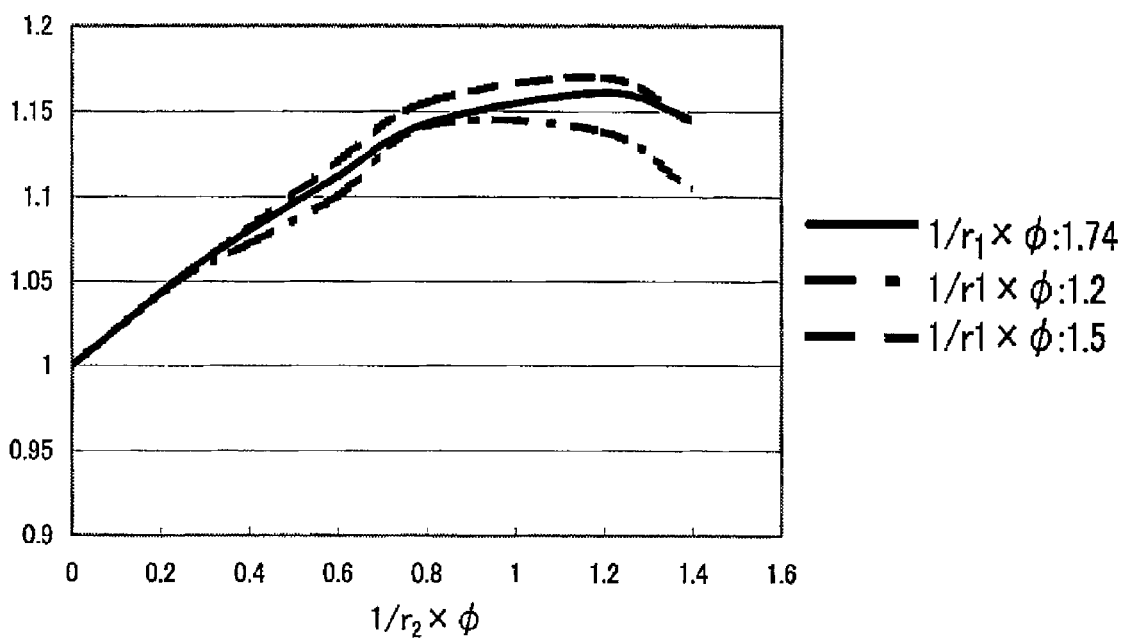
FIG. 7 is a graph showing the relation between the curvature radius of the exit face of the illumination lens and the utilization efficiency of illumination light.

FIG. 7 shows the relation between the curvature radius $r_2$ of the exit face 21b of the illumination lens 21 and the utilization efficiency of illumination light. The curvature radius $r_2$ is normalized with the lens diameter φ. The efficiency is based on a result of the quantity of illumination light integrated all over the field of irradiation. The efficiency is normalized with a value of integral on the assumption that the exit face 21b is regarded as a flat face (with the curvature radius $r_2$ infinite).

From FIG. 7, with decrease in the curvature radius $r_2$ of the exit face 21b (or with increase of $1/r_2 \times \phi$), the efficiency is improved. This is because the total reflection of light rays in the exit face 21b disappears with decrease in the curvature radius $r_2$ as described above. When $1/r_2 \times \phi$ satisfies the condition of $0.24 < 1/r_2 \times \phi$, the efficiency can be improved by 5% or more.

However, the efficiency shows a saturation tendency with respect to decrease in the curvature radius $r_2$ (or increase of $1/r_2 \times \phi$). From FIG. 7, the efficiency is saturated near the point where $1/r_2 \times \phi$ is 0.96. Further, with decrease in the curvature radius $r_2$ (or increase of $1/r_2 \times \phi$), the protrusive height $\underline{h}$ (see FIG. 2) of the lens 21 from an end face of the front end portion 14 of the insertion portion 10 increases so that the lens 21 may be exposed to external force easily, while the acting area (contact area) in which the external force acts on the lens 21 is reduced so that the lens 21 may be damaged easily. Also in consideration of user friendliness or the like, it is desired that the protrusive height $\underline{h}$ [mm] of the lens 21 satisfies h<0.15. When φ is 1.2 and $1/r_2 \times \phi$ is 0.96, $\underline{h}$ reaches about 0.15.

From the above description, it is preferable that $1/r_2 \times \phi$ is set to satisfy the relation of $0.24 < 1/r_2 \times \phi < 0.96$.

Figure 8:
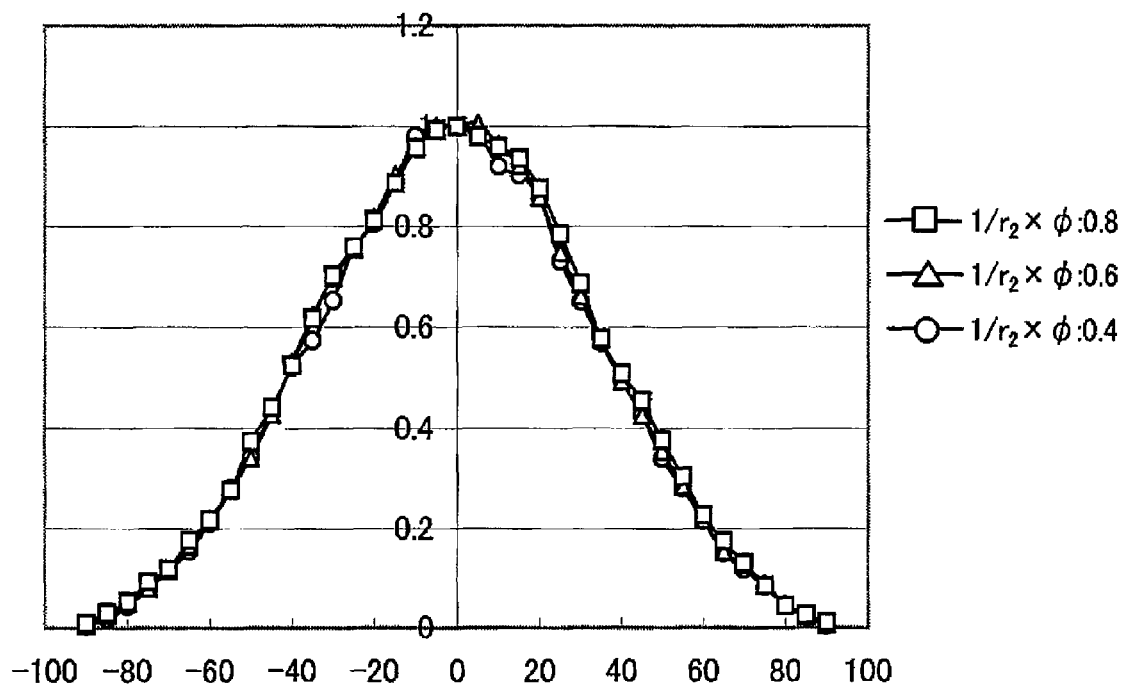
FIG. 8 is a graph showing the relation between the curvature radius of the exit face of the illumination lens and the shape of light distribution.

FIG. 8 shows the relation between the curvature radius $r_2$ of the exit face 21b of the illumination lens 21 and the shape of light distribution. The shape of light distribution is normalized with the quantity of light on the optical axis. Incidentally, $1/r_1 \times \phi$ is set at 1.74 ($r_1 = 0.69$).

It is proved from FIG. 8 that the curvature radius $r_2$ of the exit face 21b of the illumination lens 21 does not have substantial influence on the shape of light distribution when $1/r_2 \times \phi$ is in the aforementioned range.

Figure 9:
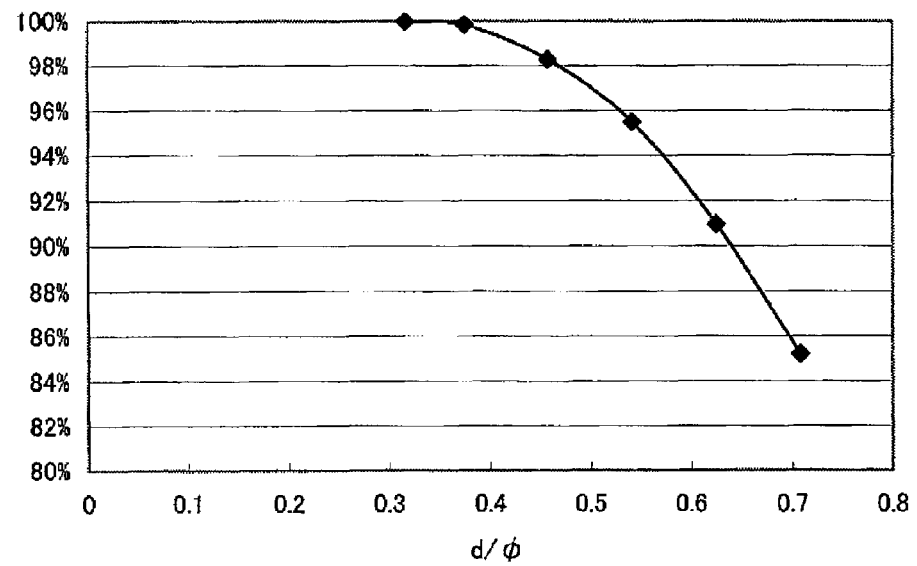
FIG. 9 is a graph showing the relation between the thickness of the illumination lens and the utilization efficiency of illumination light.

Next, consider about the thickness of the illumination lens 21. When the thickness $\underline{d}$ of the lens 21 is on or beyond a certain level with respect to the lens diameter φ of the lens 21, light rays may be kicked on the side face of the lens 21 to affect the utilization efficiency of illumination light. FIG. 9 shows the relation between the value d/φ in which the thickness d is normalized with the lens diameter φ, and the efficiency. The efficiency herein is based on the quantity of outgoing light from the lens 21, and expressed by a relative quantity of light, in which the efficiency is regarded as 100% when the lens 21 is thin enough to prevent light rays from being kicked on the side face of the lens 21. In addition, it is assumed that $1/r_1 \times \phi$ is 1.74 ($r_1=0.69$) and $1/r_2 \times \phi$ is 0.48 ($r_2=2.5$)

From FIG. 9, it is preferable that d/φ satisfies the condition of d/φ<0.5 in consideration of the rate of decrease in the efficiency. In the illumination lens of the endoscope, the lens diameter φ is typically in a range of 0.5<1<2. If lens diameter φ is not smaller than 2 mm, there is a fear that the lens diameter may impede reduction in the diameter of the endoscope. On the other hand, if the lens diameter φ is not larger than 0.5 mm, the lens may be hardly processed.

In addition, the lens diameter φ of the illumination lens 21 relative to the diameter Φ of the light guide 28 has influence on the utilization efficiency of illumination light. It is preferable that the ratio φ/Φ of the lens diameter φ to the light guide diameter Φ is in a range of 0.6<φ/Φ<0.9. When the ratio φ/Φ is not lower than 0.9, there is a fear that light rays emitted at an angle from the front end of the light guide 28 may be kicked on the side face of the lens 21 to lower the efficiency. On the other hand, when the ratio φ/Φ is not higher than 0.6, there is a fear that the number of optical fibers constituting the light guide 28 may be so small that the absolute quantity of light becomes insufficient.

As described above, this specification discloses an illumination lens disposed in a front end of a light guide of an endoscope, wherein an entrance face and an exit face of the illumination lens have positive power, and when a diameter of the lens is φ [mm], a curvature radius $r_1$ [mm] of the entrance face satisfies the following Expression (1) while a curvature radius $r_2$ [mm] of the exit face satisfies the following Expression (2).

$$1.2 < 1/r_1 \times \phi < 1.8 \tag{1}$$

$$0.24 < 1/r_2 \times \phi < 0.96 \tag{2}$$

With the aforementioned configuration, it is possible to achieve a good balance between improvement in the utilization efficiency of illumination light and the wider-angle light distribution. Further, the curvature radius of the entrance face is different from the curvature radius of the exit face, so that the entrance face and the exit face can be prevented from being disposed inside out by mistake when the illumination lens is placed in the front end of the light guide.

In addition, in the illumination lens disclosed in this specification, the entrance face serves as a light diffusing face.

In addition, in the illumination lens disclosed in this specification, the lens diameter φ [mm] satisfies the following Expression (3).

$$0.5 < \phi < 2 \tag{3}$$

In addition, in the illumination lens disclosed in this specification, the distance d [mm] between the entrance face and the exit face on the optical axis satisfies the following Expression (4).

$$d/\phi < 0.5 \tag{4}$$

In addition, an endoscope with any one of the aforementioned illumination lenses provided in a front end of a light guide is disclosed in this specification.

Description Of Reference Numerals 1 endoscope
3 processor
4 light source unit
5 monitor
10 insertion portion
11 operation portion
12 universal cord
13a connector
13b connector
14 front end portion
15 curved portion
16 flexible portion
21 illumination lens
21a entrance face
21b exit face
22 objective lens
23 imaging unit
28 light guide
29 signal line

What is claimed is:

1. An illumination lens to be disposed in a front end of a light guide of an endoscope, comprising:
an entrance face that has positive refractive power; and
an exit face that has positive refractive power,
wherein the following Expression (1) is satisfied while the following Expression (2) is satisfied $$1.2 < 1/r_1 \times \phi < 1.8, \tag{1}$$

$$0.24 < 1/r_2 \times \phi < 0.96, \tag{2}$$

where φ [mm] is a diameter of the lens,
$r_1$ [mm] is an absolute value of a curvature radius of the entrance face, and
$r_2$ [mm] is an absolute value of a curvature radius of the exit face,
wherein the entrance face includes a light diffusing face, and
wherein the illumination lens consists of one positive lens.

2. The illumination lens according to claim 1, wherein the following Expression (3) is satisfied $$0.5 < \phi < 2 \tag{3}.$$

3. The illumination lens according to claim 1, wherein the following Expression (4) is satisfied $$d/\phi < 0.5, \tag{4}$$

where d [mm] is a distance between the entrance face and the exit face on an optical axis.

4. An endoscope comprising:
a light guide;
an illumination lens that is provided in a front end of the light guide and includes:
an entrance face that has positive refractive power; and
an exit face that has positive refractive power,
wherein the following Expression (1) is satisfied while the following Expression (2) is satisfied $$1.2 < 1/r_1 \times \phi < 1.8, \tag{1}$$

$$0.24 < 1/r_2 \times \phi < 0.96, \tag{2}$$

where φ [mm] is a diameter of the lens,
$r_1$ [mm] is an absolute value of a curvature radius of the entrance face, and
$r_2$ [mm] is an absolute value of a curvature radius of the exit face, wherein the entrance face includes a light diffusing face, and wherein the illumination lens consists of one positive lens.

5. The endoscope according to claim 4, wherein the following Expression (3) is satisfied $$0.5 < \phi < 2 \qquad (3).$$

6. The endoscope according to claim 4, wherein the following Expression (4) is satisfied $$d/\phi < 0.5, \qquad (4)$$

where d [mm] is a distance between the entrance face and the exit face on an optical axis.

\* \* \* \* \*